United States Patent [19]

Sommer

[11] Patent Number: 5,033,851
[45] Date of Patent: Jul. 23, 1991

[54] LIGHT SCATTERING METHOD AND APPARATUS FOR DETECTING PARTICLES IN LIQUID SAMPLE

[75] Inventor: Holger T. Sommer, Greenbelt, Md.

[73] Assignee: Pacific Scientific Company, Newport Beach, Calif.

[21] Appl. No.: 358,573

[22] Filed: May 30, 1989

[51] Int. Cl.⁵ .......................................... G01N 21/00
[52] U.S. Cl. .................................... 356/338; 356/436
[58] Field of Search .......................... 356/335–343, 356/244, 246

[56] References Cited

U.S. PATENT DOCUMENTS

| 3,406,289 | 10/1968 | Schleusener | 356/335 |
| 3,766,489 | 10/1973 | Rosenberg et al. | 331/94.5 |
| 3,840,304 | 10/1974 | Hirafuji | 356/436 |
| 4,281,924 | 8/1981 | Auer et al. | 356/338 |
| 4,571,079 | 2/1986 | Knollenberg | 356/336 |
| 4,842,406 | 6/1989 | VonBargen | 356/336 |
| 4,854,705 | 8/1989 | Bachalo | 356/338 |

Primary Examiner—Richard A. Rosenberger
Assistant Examiner—Hoa Pham
Attorney, Agent, or Firm—Lane, Aitken & McCann

[57] ABSTRACT

A method and apparatus for detecting particles contained in a liquid sample includes using a nozzle to form the liquid sample into an unconfined stream having substantially flat sides and directing the stream into intersection with a laser beam in the external cavity of a laser, wherein the sides of the stream are oriented at the Brewster angle with respect to the laser beam. Light scattered from the laser beam by particles in the liquid stream as they pass through the laser beam is collected and directed by a lens to a photodetector which, in response to the impinging scattered light, emits signals for counting and measuring the particles contained in the liquid stream.

6 Claims, 1 Drawing Sheet

LIGHT SCATTERING METHOD AND APPARATUS FOR DETECTING PARTICLES IN LIQUID SAMPLE

BACKGROUND OF THE INVENTION

The present invention relates to a particle size measuring cell and, more particularly, to a measuring cell in which the sizes of particles entrained in a liquid stream are measured by passing the liquid stream through a laser beam and detecting the light scattered from the laser beam.

In known particle size measuring cells of the above type, individual particles in the liquid stream passing through the laser beam scatter the light toward a photodetector, which transmits a signal in response. The amount of scattered light impinging on the photodetector is proportional to the size of the particle causing the scattering, and the amplitude of the signal transmitted by the photodetector is determined by the amount of impinging light, so that the amplitude of the signal transmitted by the photodetector is a measure of the size of the particle passing through the laser beam.

The scattered light is collected by a lens and focused on the photodetector, which generates its pulses in response to each particle passing through the laser beam. The liquid stream is typically carried through the laser beam by a conduit of transparent material. As a result, there are substantial losses in the energy of the beam as it passes from air through one wall of the conduit, the fluid stream, and then the other wall of the conduit, thus, passing through numerous interfaces between various media having different indexes of refraction. Furthermore, since the conduits are typically circular in cross-section, the fluid stream is circular in cross-section and, therefore, fairly thick at the center where the laser beam intersects, thereby increasing the losses. For these reasons, prior devices for detecting and measuring particles in liquid streams have been limited to use with a laser beam emitted from a conventional laser. An external cavity laser has not been used in connection with measuring particles in liquid streams since losses in the light beam as it passed through the liquid stream have rendered it difficult, if not impossible, to maintain lasing.

SUMMARY OF THE INVENTION

By the present invention, a liquid sample containing particles to be detected is formed by a nozzle into a thin unconfined stream having flat sides and is passed at the Brewster angle through a laser beam in an external cavity of the laser. Particles in the liquid stream scatter light from the beam, and the scattered light is focused by a lens and directed to a photodetector. The use of a flat-sided free-falling stream flowing at the Brewster angle significantly reduces losses in the laser beam as it passes through the stream, thereby allowing lasing of the beam in the external cavity to be maintained. The laser beam within an external cavity of a laser is far more intense than a laser beam which has been emitted from a conventional laser. The greater intensity of the light in the beam of an external cavity laser results in stronger signals from the photodetector, which allows smaller particles to be detected and measured. Since the unconfined stream at the Brewster angle reduces losses in a laser beam enough so that lasing in an external cavity can be maintained, an external cavity laser can be employed and greater sensitivity can be achieved for detecting and measuring particles.

DETAILED DESCRIPTION OF THE PREFERRED EMBODIMENT

Figure 1:
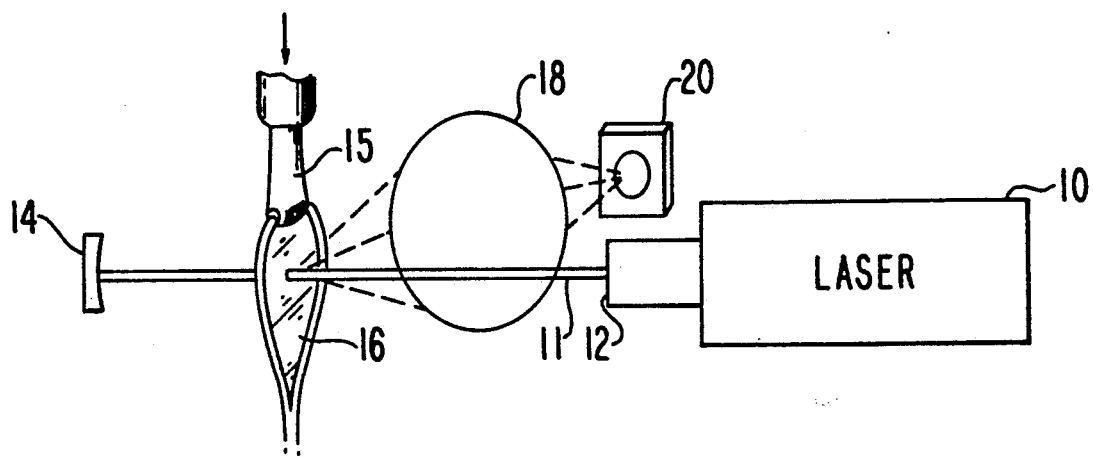
FIG. 1 is a schematic front view of the liquid stream particle size measuring cell according to the present invention.
Figure 2:
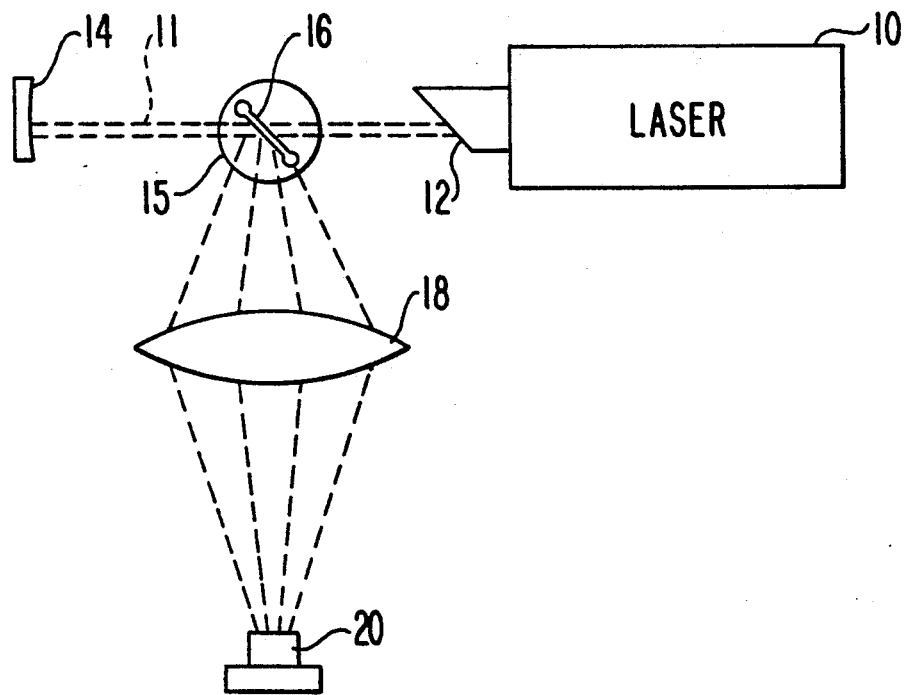
FIG. 2 is a bottom plan view of the measuring cell of FIG. 1.

As can be seen from the FIGS. 1 and 2, the liquid stream particle size measuring cell according to the present invention includes a laser 10 which projects a collimated beam of light 11 through a Brewster window 12. The light beam 11 is reflected by a concave mirror 14 back through the Brewster window 12 and into the laser 10 to define an external cavity of the laser 10.

A sample of liquid containing particles to be detected and measured is formed by a nozzle 15 into an unconfined thin stream 16 having opposed flat sides. A nozzle suitable for forming the liquid into a thin stream having substantially planar and parallel smooth surfaces is disclosed in U.S. Pat. No. 3,766,489 to Rosenberg et al. The liquid stream 16 is directed through the laser beam 11 in the external cavity of the laser 10 at the Brewster angle, so that the energy losses in the laser beam as it passes through the fluid stream are minimized. The losses are also minimized by the fact that the stream is unconfined, that is, it is not contained within a tube and does not flow along any plates, either of which would also cause losses to the laser beam, since the laser beam would be required to pass through them.

When the light of the laser beam 11 strikes a particle in the fluid stream 16, some of the light is scattered, and some of the scattered light falls on a lens 18, which collects the light and focuses it on a photodetector 20. The photodetector 20 emits a signal in response to the reception of light from the lens 18. The number of pulses of light is an indication of the number of particles in the fluid stream, and the amplitude of the signals is proportional to the amount of light scattered and received by the photodetector, which is a measure of the size of each particle.

Apparatus for processing the signals from the photodetector 20 in order to count and determine the sizes of the particles in the stream are well known in the art.

It can be appreciated from the foregoing that a particle detecting apparatus of greater sensitivity is provided by the present invention, since a more intense beam of light can be employed, which allows smaller particles to be detected than could be detected by previously known apparatus. It can further be appreciated that various modifications can be made to the above-described apparatus without departing from the spirit and scope of the present invention, which is defined in the appended claims.

I claim:

1. Apparatus for detecting particles contained in a liquid sample, comprising:
   a laser projecting a beam of light along a path;
   means positioned in said path for reflecting said beam back into said laser and defining with said laser an external laser cavity;
   means for forming the liquid sample into an unconfined stream having substantially flat sides oriented at the Brewster angle with respect to the laser beam; and a photodetector positioned to receive light scattered from the laser beam by the particles in the liquid stream which pass through the laser beam.

2. The apparatus according to claim 1, wherein said reflecting means is a mirror.

3. The apparatus according to claim 2, wherein the mirror is concave.

4. The apparatus according to claim 1, further comprising means for collecting light scattered by the particles and directing the collected light to said photodetector.

5. The apparatus according to claim 4, wherein said collecting and directing means comprises a lens.

6. A method for detecting particles contained in a liquid sample, comprising:

establishing a laser beam in an external cavity of a laser;

forming the liquid sample into an unconfined stream having substantially flat sides and directing the stream into intersection with the laser beam in the external cavity, wherein the sides of the stream are oriented at the Brewster angle with respect to the laser beam; and detecting light scattered from the laser beam by particles in the liquid stream.

* * * * *